US00PP08582P

United States Patent [19]

Warringer, deceased

[11] Patent Number: Plant 8,582

[45] Date of Patent: Feb. 8, 1994

[54] FLORIBUNDA ROSE PLANT NAMED 'JACSIMPL'

[75] Inventor: William A. Warriner, deceased, late of Tustin, Calif., by Alene B. Warringer, legal representative

[73] Assignee: Bear Creek Gardens, Inc., Medford, Oreg.

[21] Appl. No.: 883,253

[22] Filed: May 14, 1992

[51] Int. Cl.[5] ..... A01H 5/00

[52] U.S. Cl. ..... Plt./28

[58] Field of Search ..... Plt. 28, 29, 22, 20

*Primary Examiner*—Howard J. Locker

*Attorney, Agent, or Firm*—Klarquist, Sparkman, Campbell, Leigh and Whinston

[57] ABSTRACT

A floribunda rose having bright flowers, thick petals and an abundance of glands on stipules and petiole rachis. It is easily propagated by soft and hardwood cuttings and is resistant to powdery mildew and rust.

1 Drawing Sheet

The present invention relates to a new and distinct variety of rose plant of the Floribunda class which was originated by me by crossing an unnamed seedling, with the variety JACjem, U.S. Plant Pat. No. 5,001.

The primary objective of this breeding was to produce a new rose variety having the bright red color of the unnamed seedling combined with the good floribunda habit, disease resistant foliage and heavy flower production of JACjem. The objective was substantially achieved along with other desirable improvements as evidenced by the following unique combination of characteristics which are outstanding in the new variety and which distinguish it from its parents, as well as from all other varieties of which I am aware:

1. Presence of numerous glands on the petiole rachis and stipules;
2. Bright Red flower color;
3. Thick petals;
4. Ease of propagation by soft or hardwood cuttings;
5. Resistance to powdery mildew and rust.

Asexual reproduction of this new variety by buddings and softwood or hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—JACjem, U.S. Plant No. 5,001.

Classification:

*Botanical.*—Rosa hybrida.

*Commercial.*—Floribunda.

FLOWER

Observations made from specimens grown in a garden environment in Somis, Calif., from May–August 1991.

Blooming habit: Recurrent.

Bud:

*Size.*—1½ when the petals start to unfurl.

*Form.*—Long, pointed ovoid.

*Color.*—When sepals first divide, bud color is Red Group 45B. When half blown, the upper sides of the petals are Red Group 45B; and the lower sides of the petals are Red Group 45B.

*Sepals.*—Color: Green Group 138C. Surface texture: Covered in fine hairs. There are three lightly appendaged sepals. There are two unappendaged sepals with hairy edges.

*Receptacle.*—Color: Green Group 141C. Shape: Funnel. Size: Small, ⅜"×⅜". Surface: Smooth with very fine hairs and a few glands.

*Peduncle.*—Length: Medium, 2½" Surface: Glandular. Color: Medium green. Strength: Bending.

Bloom:

*Size.*—Medium. Average open size is 3½–4".

*Borne.*—Singly and several together in clusters. If in clusters: Rounded.

*Stems.*—Short (8–10").

*Form.*—When first open: High centered. Permanence: Flattens, outer petal edges curl slightly.

*Petalage.*—Number of petals under normal conditions: 20–25.

*Color.*—The upper side of the petals is Red Group 45B. The reverse side of the petals is Red Group 45B. The base of the petals has a small whitish green half moon at the point of attachment. The major color on the upper side Red Group 45B.

*Variegations.*—Occasional white streak on the guard petals.

*Discoloration.*—The general tonality at the end of the first day: No change. At the end of the third day, No change.

*Fragrance.*—Moderate.

Petals:

*Texture.*—Thick.

*Shape.*—Round.

*Form.*—Tips slightly recurved.

*Arrangement.*—Imbricated, with a few petaloids in the center.

*Persistence.*—Drop off cleanly.

*Lastingness.*—On the plant: Fair, 4–5 days. As a cut flower: Fair, 5 days.

Reproductive parts:

*Anthers.*—Size: Medium. Quantity: Many. Color: Yellow. Arrangement: Regular around styles, mixed with occasional petaloids.

*Filaments.*—Color: Whitish green.

*Pollen.*—Color: Lemon yellow.

*Styles.*—Color: Red.

*Stigmas.*—Color: Greenish white.

Form: Bush.

Growth: Vigorous; upright; branching. Foliage: Number of leaflets on normal mid-stem leaves: 5 or 7.

*Size.*—Large, 5½–4".

*Quantity.*—Abundant.

*Color.*—New foliage: Reddish. Old foliage: Dark glossy green.

Leaflets:

*Shape.*—Pointed oval.

*Texture.*—Upper side: Leathery, glossy.

*Edge.*—Serrated.

*Serration.*—Single, small.

*Petiole rachis.*—Color: Green. Petiole has numerous glands on the upper rib surface.

*Petiole underside.*—Rough with prickles.

*Stipules.*—Medium, bearded and have many glands.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by the unique combination of its bright red flower color, thick petals, abundance of glands on stipules and petiole rachis, ease of propagation by soft and hardwood cuttings and its resistance to powdery mildew and rust.

* * * * *

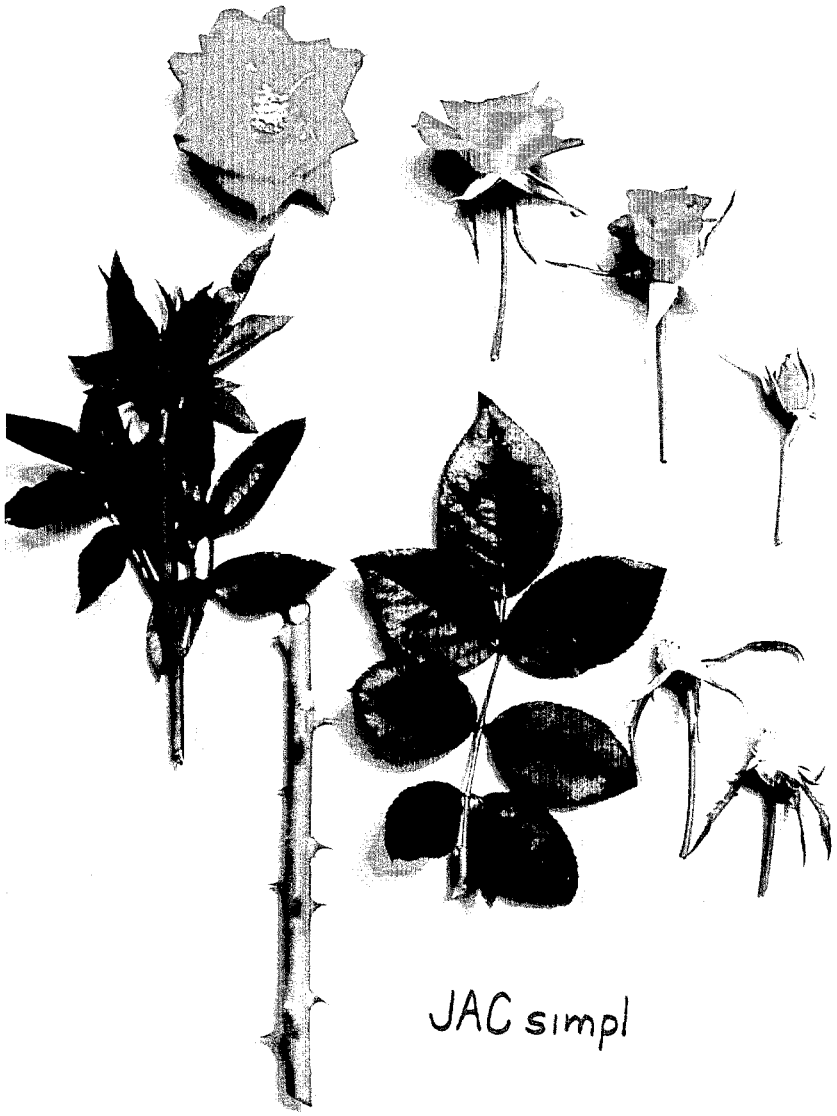
JAC simpl